United States Patent [19]

Ohlinger et al.

[11] 4,260,554
[45] Apr. 7, 1981

[54] STORAGE-STABLE, LIQUID CARBODIIMIDE MODIFIED POLYISOCYANATES AND PROCESS FOR THEIR MANUFACTURE

[75] Inventors: Rainer Ohlinger, Heidelberg; Georg Falkenstein, Neustadt; Rolf Wurmb, Heidelberg; Matthias Marx, Bad Duerkheim, all of Fed. Rep. of Germany

[73] Assignee: BASF Aktiengesellschaft, Ludwigshafen, Fed. Rep. of Germany

[21] Appl. No.: 70,282

[22] Filed: Aug. 27, 1979

[30] Foreign Application Priority Data

Aug. 30, 1978 [DE] Fed. Rep. of Germany ....... 2837770

[51] Int. Cl.³ .......................................... C07C 119/042
[52] U.S. Cl. ...................... 260/453 SP; 260/453 AL; 260/453 AR; 260/453 A
[58] Field of Search ................... 260/453 SP, 453 AL, 260/453 AR; 453 A

[56] References Cited

U.S. PATENT DOCUMENTS

| | | | |
|---|---|---|---|
| 2,941,966 | 6/1960 | Campbell | 260/453 SP |
| 3,384,653 | 5/1968 | Erner | 260/453 SP |
| 3,640,966 | 2/1972 | Henning et al. | 260/453 SP |
| 4,014,935 | 3/1977 | Ibbotson | 260/453 SP |
| 4,088,665 | 5/1978 | Findeisen et al. | 260/453 SP |
| 4,120,884 | 10/1978 | Woerner et al. | 260/453 SP |

FOREIGN PATENT DOCUMENTS 1404301 9/1972 United Kingdom ............... 260/453 SP Primary Examiner—Henry R. Jiles
Assistant Examiner—Robert C. Whittenbaugh
Attorney, Agent, or Firm—Norbert M. Lisicki

[57] ABSTRACT

Storage-stable, liquid carbodiimide-modified polyisocyanates are prepared by condensation of polyisocyanates in the presence of catalytic amounts of phospholine, phospholidine, phospholine oxides and/or phospholidine oxides, said condensation terminated and the products stabilized by means of perchloric acid or trifluoromethanesulfonic acid.

7 Claims, No Drawings

STORAGE-STABLE, LIQUID CARBODIIMIDE MODIFIED POLYISOCYANATES AND PROCESS FOR THEIR MANUFACTURE

BACKGROUND OF THE INVENTION

1. Field of the Invention

The present invention concerns storage-stable, liquid carbodiimide-modified polyisocyanates having isocyanate contents of approximately 20 to 45 percent by weight based on the total weight and a process for their manufacture.

2. Description of the Prior Art

The manufacture of carbodiimide-modified polycondensation products is known according to the data in German Pat. No. 1,130,594. Organic, low molecular compounds containing at least two isocyanate groups are condensed in the presence of 0.01 to 10 percent by weight, based on the weight of the polyisocyanate, of phospholines or phospholidines or their oxides, as catalysts, at temperatures ranging from room temperature to 300° C. The carbodiimide-modified polycondensation products have average molecular weights of at least 750 and may be used for the manufacture of molded materials, fibers, films and foils.

According to German Published Application No. 2 245 634, adducts consisting of phospholine oxides, phospholine sulfides, phospholane oxides or phospholane sulfides with monoalcohols, dialcohols and/or polyalcohols of molecular weights from 32 to 250, protic acids, metal salts or acid chlorides are described as catalysts for the manufacture of foams containing carbodiimide groups.

Due to their high activity, these catalysts are very well suited for the manufacture of foam and resins containing carbodiimide groups but not for the manufacture of polyisocyanates containing carbodiimide groups.

According to data in German Patent Application No. 1,668,083, polyisocyanates possessing carbodiimide-isocyanate adducts are prepared by heating organic polyisocyanates in the presence of 0.01 to 10 mole percent based on organic compounds of a biuret, urea, amide, urethane, allophonate, isocyanurate, uretidione or uretonimine as catalysts to above 150° C. and cooling the resulting reaction products to room temperature.

Storage-stable, liquid isocyanate adducts based on 4,4'-diphenylmethane diisocyanates are also produced in accordance with German Patent Application No. 1,593,619 by heating said diisocyanate to temperatures of 160° to 250° C. in the presence of 0.1 to 3 percent by weight of a trialkyl phosphate, trialkenyl phosphate, triaralkyl phosphate, triaryl phosphate, tricycloalkyl phosphate or tricycloalkenyl phosphate. The drawback of this process is that the condensation must be carried out in the presence of relatively large amounts of catalyst at temperatures above 150° C. resulting in numerous by-products, for example, isocyanurate by-products, which are formed in addition to the desired adducts possessing carbodiimide groups. These condensation products have low storage stability since the reaction is stopped merely by cooling the reaction mixture. Thus, the condensation continues at room temperature albeit at a slower rate.

Further disadvantages are that the carbodiimide adducts are relatively dark due to the high reaction temperatures and that suspended therein are variable amounts of solids as by-products which must be removed at additional processing costs.

In order to avoid these drawbacks, processes are described in German Published Application Nos. 2,537,685; 2,606,419 and 2,614,323, wherein condensation occurs in the presence of phospholines, phospholidines and/or their oxides at temperatures below 200° C. and is terminated by adding hydrogen halides, sulfur and phosphorus halide compounds, organic acid halides, Lewis acids, alkyl sulfates and toluenesulfonic acid esters, metal-II and metal-III halides, and silica-based adsorbents.

Using these procedures, it is possible to produce room temperature stable carbodiimide-modified polyisocyanates. The disadvantage of this process, however, is that the phospholine oxide salts and/or adducts formed during the terminating process act as carbodiimide-producing catalysts for isocyanates so that the polycondensation is renewed at slightly increased temperatures and/or must be removed by employing, among others, such solid absorbing substrates as animal charcoal, diatomaceous earth, Fuller's earth, and zeolite.

The purpose of this invention, therefore, was to produce stable, liquid, nearly colorless carbodiimide-modified polyisocyanates under relatively mild reaction conditions which do not exhibit the above-described disadvantages.

SUMMARY OF THE INVENTION

This invention relates to storage-stable liquid carbodiimide-modified polyisocyanates and to a process for their manufacture by condensation of polyisocyanates in the presence of catalytic amounts of phospholine, phospholidine, phospholine oxides and/or phospholidine oxides wherein the condensation is terminated and at the same time stabilized by means of perchloric acid or trifluoromethanesulfonic acid upon reaching an NCO content of approximately 20 to approximately 45 percent by weight based on the total weight of the polyisocyanate.

The carbodiimide-modified polyisocyanates, according to this invention, have the advantage that they contain extremely small amounts of catalysts, essentially no by-products and that they are only slightly colored or are even nearly colorless due to the mild reaction conditions. Furthermore, this process is extremely economical since no equipment is required in order to quickly cool the reaction mixture from temperatures of greater than 200° C. to below 100° C. as taught by the prior art.

DESCRIPTION OF THE PREFERRED EMBODIMENT

In accordance with the invention, the condensation is carried out in the presence of catalytic amounts of the catalysts listed below with the amount of catalyst being dependent upon the reactivity of the respective catalyst and the polyisocyanate and which can be determined easily by simple tests well known to those skilled in the art. Surprisingly, it was found that the required amount of catalyst can be extremely low compared with the catalyst concentration requirement of the current state-of-the-art. The catalyst is generally employed in an amount from 0.1 to 100 ppm, preferably from 1 to 10 ppm, based on the weight of organic polyisocyanate. If the catalysts are used in greater quantities, the carbodiimide formation takes place extremely quickly and it is very difficult to stabilize the resulting end products.

For the manufacture of carbodiimide-modified polyisocyanates according to the invention, the polyisocyanates may be condensed either in bulk or in solution, preferably in bulk. Any inert organic solvent may be employed when the condensation is carried out in solution. Examples include aromatic compounds such as benzene, chlorobenzene, dichlorobenzene, trichlorobenzene, toluene, xylene, as well as nitromethane, acetonitrile, methylethylketone, methylamylketone, dibutyl ether, anisole, methylene chloride and perchloroethylene.

The condensation is generally carried out at temperatures of 20° to about 200° C. The aliphatic, cycloaliphatic and araliphatic diisocyanates are preferably reacted at temperatures of 100° to 200° C. and the aromatic diisocyanates are preferably reacted at temperatures of from 60° to 120° C., and more preferably from 90° to 110° C. The condensation may also be carried out at higher temperatures. This, however, does not afford any advantages.

Since carbon dioxide is evolved during the carbodiimide formation with a loss of NCO groups, the course of the reaction may be followed, for instance, by continuous monitoring of the isocyanate content or through measurement of the amount of carbon dioxide evolved. After reaching a certain isocyanate content, which requires condensation times of 10 minutes to 24 hours, preferably 1 hour to 6 hours depending on the starting components and reaction parameters, the formation of carbodiimide is terminated and the carbodiimide-modified polyisocyanate is simultaneously stabilized.

For this purpose, perchloric acid or, preferably, trifluoromethanesulfonic acid, is added to the reaction mixture as terminating and stabilizing agent in accordance with the invention. The concentration of said agent may be varied within wide limits based on the amount of catalyst used. However, the quantity ratio of catalyst to termination and stabilization agent is not only a function of the reactivity of the polyisocyanates and the catalyst but also of the agent used. Based on the concentration of catalyst, from 1 to about 100, preferably from 2 to about 10, parts by weight of the termination and stabilization agent per part by weight of catalyst are generally used.

Suitable for the manufacture of carbodiimide-modified polyisocyanates are all aliphatic, cycloaliphatic, araliphatic, and preferably aromatic polyisocyanates. For example, these include aliphatic diisocyanates such as tetramethylene diisocyanate, decamethylene diisocyanate, and, preferably, hexamethylene diisocyanate; cycloaliphatic diisocyanates such as 1,4-cyclohexyl diisocyanate, 1-methylcyclohexyl-2,4- or 2,6-diisocyanate, isophorone diisocyanate, 2,2'-2,4' and 4,4'-diisocyanatodicyclohexylmethane; araliphatic diisocyanates such as alpha,alpha'-xylylene diisocyanate and, preferably, aromatic diisocyanates such as 2,4-and 2,6-toluene diisocyanate and isomer mixtures thereof, 2,2'-, 2,4'- and 4,4'- -diphenylmethane diisocyanate and isomer mixtures thereof as well as polyphenylene polymethylene polyisocyanates and mixtures of diphenylmethane diisocyanate and polyphenylene polymethylene polyisocyanates. Preferably used are mixtures consisting of 4,4'-diphenylmethane diisocyanate and 2,4- and 2,6-toluene diisocyanates (80:20) weight ratio as well as pure 4,4'-diphenylmethane diisocyanate alone. The listed polyisocyanates may be used individually or in the form of mixtures.

Possible catalysts for the manufacture of carbodiimide polyisocyanates include phospholines, phospholidines and/or their oxides. The appropriate phospholines and phospholidines may be produced by reduction of the corresponding dichlorophospholines or phospholidines with lithium aluminum hydrides. These dichloro compounds are also used in the manufacture of phospholine oxides and are described, for instance, in U.S. Pat. No.2,663,736. Phospholine oxides are described in U.S. Pat. Nos. 2,663,737 and 2,663,738, and phospholidine oxides are described in U.S. Pat. No. 2,663,739. Examples of suitable catalysts include: phospholines such as 1-phenyl-3-phospholine, 3-methyl-1-phenyl-3-phospholine, 1-ethyl-3-phospholine, 3-isopropyl-1-phenyl-3-phospholine, and 3-(4-methyl-3-pentenyl)-1-phenyl-3-phospholine; phospholine oxides such as 3-methyl-1-phenyl-3-phospholine-1-oxide, 1-ethyl-3-methyl-3-phospholine-1-oxide, 1-ethylphenyl-3-methyl-3-phospholine-1-oxide, 3-(4-methyl-3-pentenyl)-1-phenyl-3-phospholine-1-oxide, 3-chloro-1-phenyl-3-phospholine-1-oxide and 1,3-phenyl-3-phospholine-1-oxide. Examples of typical phospholidines include1-phenylphospholidine, 3-phenyl-1-phenylphospholidine, 1-ethyl-3-methylphospholidine, and 1-ethyl-phospholidine. Suitable phospholidine oxides include 1-ethyl-3-methyl-phospholidine-1-oxide and 1-phenyl-phospholidine-1-oxide.

Preferably used as catalysts are: 1-phenyl-3-methylphospholine-1-oxide, 1-methyl-phospholine-1-oxide and 1-phenyl-3methylphospholine.

In order to achieve a certain carbodiimide content, the organic polyisocyanates are preferably reacted until the carbodiimide-modified polyisocyanate solution has the desired NCO content which can be easily determined by analytical methods. However, it is also possible to continue the reaction further and obtain the desired NCO content by addition of fresh polyisocyanates.

The carbodiimide-modified polyisocyanates according to this invention have isocyanate contents of 20 to 45 percent by weight, preferably of 28 to 31 percent by weight, and vicosities of 20 to 300, preferably of 20 to 100, centipoises at 20° C. These products have excellent storage stability, are liquid, nearly colorless and do not tend toward crystallization at room temperature. In combination with polyols, for instance, such as polyesters, polyethers, polyacetals, and others containing hydroxyl groups, they are very well suited for the manufacture of foams, coatings, adhesives and elastomers.

The following Examples are provided to further illustrate the invention. The parts referred to in the Examples are parts by weight.

EXAMPLE 1

A 4-liter glass reactor equipped with agitator, thermometer, and reflux condenser was charged with 3000 grams of diphenylmethane diisocyanate (NCO content 33.6 percent) consisting of at least 97 percent of 4,4'-isomer and 3 percent of 2,4'-isomer and heated to 100° C. At this temperature, 15 milligrams of 1-phenyl-3-methyl-3-phospholine-1-oxide was added and the reaction temperature was increased to 110° C. After 1.57 hours, the NCO content dropped to 30.2 percent with an evaluation of $CO_2$. The reaction mass was then cooled to room temperature within 15 minutes under reduced pressure. The NCO content of the liquid product was found to be 29.9 percent.

To 700 grams of the carbodiimide-modified diphenylmethane diisocyanate produced in this manner was added 53 milligrams of trifluoromethanesulfonic acid. The storage stability of the product was measured at room temperature and 80° C.

After 4 weeks, the NCO content of the sample stored at room temperature had dropped to 29.4 percent. This corresponds with the conversion of the carbodiimide into uretonimine which occurs at room temperature. A further evolution of carbon dioxide was not detected.

The sample stored at 80° C. showed an NCO content of 28.8 percent after being stored for 7 days.

COMPARATIVE EXAMPLE A

To 700 grams of the carbodiimide-modified diphenylmethane diisocyanate produced according to Example 1 was added 0.35 grams of benzoyl chloride which was also stored at 80° C. for 7 days. After 7 days, the NCO content of this sample was 20.0 percent.

Example 1, quenched with the deactivator according to this invention, thus displays an improved storage stability as compared with the current state-of-the-art.

EXAMPLE 2

In accordance with the procedure of Example 1, 3000 grams of diphenylmethane diisocyanate were reacted with 15 milligrams of 1-phenyl-3-methyl-3-phospholine oxide until an NCO content of 30.9 percent was reached. To 600 grams of this batch was added 18 milligrams of 70 percent perchloric acid and the mixture was stored at 80° C. for 7 days. After this period of time, the NCO content was 27.45 percent.

EXAMPLE 3

To 2000 grams of diphenylmethane diisocyanate was added 10 milligrams of 1-phenyl-3-methyl-3-phospholine oxide. The mixture was partially carbodiimized by heating at 110° C. for two hours and 30 minutes. After cooling and stabilizing with 78 milligrams of trifluromethane sulfonic acid, the product had an NCO content of 28 percent.

The product was subsequently mixed with 1440 grams of diphenylmethane diisocyanate (NCO content 33.6 percent) and an NCO content of 30.4 percent was thus achieved. Following this, a sample of this mixture, which was liquid at room temperature, was stored at 60° C. for seven days. After this storage, the NCO content was 30.1 percent.

EXAMPLE 4

To 1000 grams of hexamethylene diisocyanate (NCO content 50 percent) was added 100 milligrams of 1-phenyl-3-methyl-3-phospholine oxide and partially carbodiimized by heating at 200° C. for 2.5 hours. After cooling to room temperature, the NCO content of the product was 40.3 percent. The product was stabilized with 0.85 milligrams trifluoromethane sulfonic acid and was stored at 80° C. for seven days. Following this storage period, the NCO content was 39.5 percent.

EXAMPLE 5

To 1000 grams of isophorene diisocyanate (NCO content 37.8 percent) was added 100 milligrams of 1-phenyl-3-methyl-3-phospholine oxide and were partially carbodiimized by heating at 210° C. for two hours. After cooling and mixing with 0.85 milligrams trifluoromethane sulfonic acid, the NCO content was 31.5 percent. The product was stored at 80° C. for seven days. The resulting NCO content was 30.4 percent.

The embodiments of this invention in which an exclusive privilege or property is claimed are as follows:

1. Storage-stable, liquid carbodiimide-modified polyisocyanate having an NCO content from about 20 to about 45 weight percent, based on the total weight of said polyisocyanate prepared by condensation of a polyisocyanate in the presence of catalytic amounts of a catalyst selected from the group consisting of phospholine, phospholidine, phospholine oxide and phospholidine oxide, said condensation terminated and said carbodiimide-modified polyisocyanate stabilized by trifluoromethanesulfonic acid.

2. The storage-stable, liquid carbodiimide-modified polyisocyanates of claim 1 wherein the polyisocyanate is 4,4'-diphenylmethanediisocyanate.

3. In a process for the manufacture of storage-stable liquid carbodiimide-modified polyisocyanate prepared by condensation of a polyisocyanate in the presence of catalytic amounts of a catalyst selected from the group consisting of phospholine, phospholidine, phospholine oxide and phospholidine oxide, the improvement consisting of terminating said condensation and stabilizing said carbodiimide-modified polyisocyanate by trifluoromethanesulfonic acid.

4. The process of claim 3 wherein the carbodiimide-modified polyisocyanate polycondensation has an NCO content of 20 to 45 weight percent based on the total weight of said polyisocyanate.

5. The process of claim 3 wherein the phospholines, phospholidines, phospholine oxides and/or phspholidine oxides are used in quantities from 1 to about 100 ppm based on the weight of the polyisocyanate.

6. The process of claim 3 wherein the amount of trifluoromethanesulfonic acid used for terminating the condensation is from 1 to about 100 times the amount of catalyst.

7. The process of claim 3 wherein 4,4'-diphenylmethanediisocyanate is the polyisocyanate and trifluoromethanesulfonic acid is used for terminating the condensation process.

* * * * *